US008871232B2

(12) United States Patent
Martin et al.

(10) Patent No.: US 8,871,232 B2
(45) Date of Patent: Oct. 28, 2014

(54) SELF-INDICATING WIPE FOR REMOVING BACTERIA FROM A SURFACE

(75) Inventors: Stephanie M. Martin, Woodstock, GA (US); John Gavin MacDonald, Decatur, GA (US); Bao Trong Do, Decatur, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1142 days.

(21) Appl. No.: 11/955,696

(22) Filed: Dec. 13, 2007

(65) Prior Publication Data

US 2009/0155327 A1  Jun. 18, 2009

(51) Int. Cl.
| | |
|---|---|
| A01N 59/06 | (2006.01) |
| A01N 59/16 | (2006.01) |
| A01N 25/34 | (2006.01) |
| A01P 1/00 | (2006.01) |
| A61L 2/28 | (2006.01) |
| A47L 13/16 | (2006.01) |
| A61L 2/238 | (2006.01) |

(52) U.S. Cl.
CPC . *A61L 2/28* (2013.01); *A47L 13/16* (2013.01); *A61L 2/238* (2013.01)
USPC .......................... 424/404; 424/646; 424/682

(58) Field of Classification Search
USPC ........................................................ 424/404
See application file for complete search history.

(56) References Cited

U.S. PATENT DOCUMENTS

| | | |
|---|---|---|
| 3,338,992 A | 8/1967 | Kinney |
| 3,341,394 A | 9/1967 | Kinney |
| 3,494,821 A | 2/1970 | Evans |
| 3,502,538 A | 3/1970 | Peterson |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 4,041,203 A | 8/1977 | Brock et al. |
| 4,076,673 A | 2/1978 | Burkholder, Jr. |
| 4,100,324 A | 7/1978 | Anderson et al. |
| 4,144,370 A | 3/1979 | Boulton |
| 4,215,682 A | 8/1980 | Kubik et al. |
| 4,285,343 A | 8/1981 | McNair |
| 4,340,563 A | 7/1982 | Appel et al. |
| 4,375,448 A | 3/1983 | Appel et al. |
| 4,375,718 A | 3/1983 | Wadsworth et al. |
| 4,494,278 A | 1/1985 | Kroyer et al. |
| 4,592,815 A | 6/1986 | Nakao |
| 4,608,047 A | 8/1986 | Mattingly |
| 4,666,647 A | 5/1987 | Enloe et al. |
| 4,687,478 A | 8/1987 | Van Tilburg |
| 4,704,116 A | 11/1987 | Enloe |
| 4,708,870 A | 11/1987 | Pardini |
| 4,741,941 A | 5/1988 | Englebert et al. |
| 4,766,029 A | 8/1988 | Brock et al. |
| 4,775,582 A | 10/1988 | Abba et al. |
| 4,798,603 A | 1/1989 | Meyer et al. |
| 4,818,464 A | 4/1989 | Lau |
| 4,818,598 A | 4/1989 | Wong |
| 4,833,003 A | 5/1989 | Win et al. |
| 4,853,281 A | 8/1989 | Win et al. |
| 4,874,659 A | 10/1989 | Ando et al. |
| 4,886,512 A | 12/1989 | Damico et al. |
| 4,921,701 A | 5/1990 | Blehm Blank |
| 4,927,582 A | 5/1990 | Bryson |
| 4,950,264 A | 8/1990 | Osborn, III |
| 4,987,632 A * | 1/1991 | Rowe et al. ................. 15/104.93 |
| 5,009,653 A | 4/1991 | Osborn, III |
| 5,057,361 A | 10/1991 | Sayovitz et al. |
| 5,085,654 A | 2/1992 | Buell |
| 5,143,679 A | 9/1992 | Weber et al. |
| 5,151,092 A | 9/1992 | Buell et al. |
| 5,167,897 A | 12/1992 | Weber et al. |
| 5,169,706 A | 12/1992 | Collier et al. |
| 5,176,668 A | 1/1993 | Bernardin |

(Continued)

FOREIGN PATENT DOCUMENTS

| | | |
|---|---|---|
| AU | 510720 B | 11/1979 |
| CA | 19851180622 | 1/1985 |

(Continued)

OTHER PUBLICATIONS

Search Report and Written Opinion for PCT/IB2008/053709 dated Apr. 2, 2009, 13 pages.
Abstract of Chinese Patent No. CN1147575 dated Apr. 16, 1997.
Abstract of Japanese Patent No. JP4119169 dated Apr. 20, 1992.
Abstract of Japanese Patent No. JP4197409 dated Jul. 17, 1992.
Abstract of Japanese Patent No. JP5226187 dated Sep. 3, 1993.
Krema, R., et al. "What's New in Highloft Production?" *Nonwovens Industry*, Oct. 1997: pp. 74-78.
Fairhust, D., et al "Zeta Potential Measurements of Irregular Shape Solid Materials" *Particle Size Distribution II, Assessment and Characterization*, ACS Symposium Series 472, ISBN 0-8412-2117-0, 1991: pp. 337-353.
Cost, Frank "Pocket Guide to Digital Printing," Delmar Publishers, Albany New York, 1977: pp. 144-145.
"Colour and Constitution of Organic Molecules" Academic Press, London, Published 1976.

(Continued)

*Primary Examiner* — Audrea Buckley
(74) *Attorney, Agent, or Firm* — Dority & Manning, P.A.

(57) ABSTRACT

A wipe that includes a bacteriostatic agent that contains cations having an affinity for the negatively charged cell walls of bacteria is provided. The affinity of the bacteriostatic agent for the bacteria allows the wipe to capture bacteria, thereby removing them from a surface and also inhibiting their spread to other surfaces that may contact the wipe. Of particular advantage, the bacteriostatic agent may help protect against the spread or infection of pathogens without the use of chemicals, such as antiseptics or antibiotics. Still further, the wipe of the present invention also contains a solvatochromatic indicator that undergoes a color change in the presence of a broad spectrum of bacteria. Thus, when the wipe captures bacteria, the indicator undergoes a color change that signals to the user that the wipe is functioning properly. The lack of a color change may likewise provide the user with the assurance that the area is generally free of bacteria and clean.

14 Claims, No Drawings

(56) References Cited

U.S. PATENT DOCUMENTS

| | | | |
|---|---|---|---|
| 5,176,672 | A | 1/1993 | Bruemmer et al. |
| 5,190,563 | A | 3/1993 | Herron et al. |
| 5,192,606 | A | 3/1993 | Proxmire et al. |
| 5,196,000 | A | 3/1993 | Clear et al. |
| 5,197,959 | A | 3/1993 | Buell |
| 5,217,576 | A | 6/1993 | Van Phan |
| 5,267,992 | A | 12/1993 | Van Tilburg |
| 5,284,703 | A | 2/1994 | Everhart et al. |
| 5,300,167 | A | 4/1994 | Nohr et al. |
| 5,308,346 | A | 5/1994 | Sneller et al. |
| 5,342,342 | A | 8/1994 | Kitaoka |
| 5,350,624 | A | 9/1994 | Georger et al. |
| 5,382,400 | A | 1/1995 | Pike et al. |
| 5,401,446 | A | 3/1995 | Tsai et al. |
| 5,407,600 | A | 4/1995 | Ando et al. |
| 5,464,688 | A | 11/1995 | Timmons et al. |
| 5,486,166 | A | 1/1996 | Bishop et al. |
| 5,490,846 | A | 2/1996 | Ellis et al. |
| 5,509,914 | A | 4/1996 | Osborn, III |
| 5,509,915 | A | 4/1996 | Hanson et al. |
| 5,527,171 | A | 6/1996 | Soerensen |
| 5,540,332 | A | 7/1996 | Kopacz et al. |
| 5,558,659 | A | 9/1996 | Sherrod et al. |
| 5,569,234 | A | 10/1996 | Buell et al. |
| 5,634,916 | A | 6/1997 | Lavon et al. |
| 5,649,916 | A | 7/1997 | DiPalma et al. |
| 5,667,635 | A | 9/1997 | Win et al. |
| 5,702,378 | A | 12/1997 | Widlund et al. |
| 5,709,798 | A | 1/1998 | Adiletta |
| 5,716,349 | A | 2/1998 | Taylor et al. |
| 5,756,111 | A | 5/1998 | Yoshikawa et al. |
| 5,785,179 | A | 7/1998 | Buczwinski et al. |
| 5,853,883 | A | 12/1998 | Nohr et al. |
| 5,858,515 | A | 1/1999 | Stokes et al. |
| 5,888,524 | A | 3/1999 | Cole |
| 5,964,351 | A | 10/1999 | Zander |
| 5,964,742 | A | 10/1999 | McCormack et al. |
| 5,968,488 | A | 10/1999 | Wachter et al. |
| 5,976,168 | A | 11/1999 | Dunshee et al. |
| 6,001,303 | A | 12/1999 | Haynes et al. |
| 6,028,018 | A | 2/2000 | Amundson et al. |
| 6,030,331 | A | 2/2000 | Zander |
| 6,110,158 | A | 8/2000 | Kielpikowski |
| 6,150,002 | A | 11/2000 | Varona |
| 6,158,614 | A | 12/2000 | Haines et al. |
| 6,165,965 | A * | 12/2000 | Schalitz et al. ............... 510/384 |
| 6,183,763 | B1 * | 2/2001 | Beerse et al. ............... 424/404 |
| 6,197,404 | B1 | 3/2001 | Varona |
| 6,231,719 | B1 | 5/2001 | Garvey et al. |
| 6,269,969 | B1 | 8/2001 | Huang et al. |
| 6,269,970 | B1 | 8/2001 | Huang et al. |
| 6,273,359 | B1 | 8/2001 | Newman et al. |
| 6,315,864 | B2 | 11/2001 | Anderson et al. |
| 6,330,735 | B1 | 12/2001 | Hahn et al. |
| 6,417,120 | B1 | 7/2002 | Mitchler et al. |
| 6,440,437 | B1 | 8/2002 | Krzysik et al. |
| 6,511,465 | B1 | 1/2003 | Freiburger et al. |
| 6,531,531 | B1 | 3/2003 | Han |
| 6,607,994 | B2 | 8/2003 | Soane et al. |
| 6,613,729 | B1 | 9/2003 | Cole et al. |
| 6,617,362 | B1 | 9/2003 | Ryu et al. |
| 6,630,096 | B2 | 10/2003 | Venturino et al. |
| 6,635,755 | B1 | 10/2003 | Jaschinski et al. |
| 6,663,611 | B2 | 12/2003 | Blaney et al. |
| 6,673,447 | B2 | 1/2004 | Wei et al. |
| 6,888,044 | B2 | 5/2005 | Fell et al. |
| 6,897,168 | B2 | 5/2005 | Branham et al. |
| 7,141,518 | B2 | 11/2006 | MacDonald et al. |
| 7,282,349 | B2 | 10/2007 | Lye et al. |
| 7,399,608 | B2 | 7/2008 | MacDonald et al. |
| 2002/0102289 | A1 | 8/2002 | Drucks et al. |
| 2002/0177828 | A1 | 11/2002 | Batich et al. |
| 2003/0120253 | A1 | 6/2003 | Wentzel et al. |
| 2003/0203009 | A1 | 10/2003 | MacDonald |
| 2004/0009141 | A1 | 1/2004 | Koenig et al. |
| 2004/0060112 | A1 | 4/2004 | Fell et al. |
| 2005/0084412 | A1 | 4/2005 | MacDonald et al. |
| 2005/0084438 | A1 | 4/2005 | Do et al. |
| 2005/0084464 | A1 | 4/2005 | McGrath et al. |
| 2005/0084474 | A1 | 4/2005 | Wu et al. |
| 2005/0085144 | A1 | 4/2005 | MacDonald et al. |
| 2005/0130253 | A1 * | 6/2005 | Lye et al. ............... 435/29 |
| 2005/0136238 | A1 * | 6/2005 | Lindsay et al. ............... 428/304.4 |
| 2005/0137540 | A1 | 6/2005 | Villanueva et al. |
| 2005/0244352 | A1 | 11/2005 | Lemoine et al. |
| 2006/0008442 | A1 | 1/2006 | MacDonald et al. |
| 2006/0114754 | A1 | 6/2006 | MacDonald et al. |
| 2006/0127457 | A1 * | 6/2006 | Buchalter ............... 424/443 |
| 2007/0066482 | A1 | 3/2007 | Thijssen et al. |
| 2007/0093894 | A1 | 4/2007 | Darouiche |
| 2007/0134337 | A1 | 6/2007 | Villanueva et al. |
| 2007/0141130 | A1 | 6/2007 | Villanueva et al. |
| 2007/0141934 | A1 | 6/2007 | Sayre et al. |
| 2007/0142262 | A1 | 6/2007 | Sayre et al. |
| 2008/0147029 | A1 | 6/2008 | Pate et al. |

FOREIGN PATENT DOCUMENTS

| | | |
|---|---|---|
| DE | 1013557 A1 | 7/2001 |
| EP | 1291460 A1 | 3/2003 |
| EP | 0794223 | 9/2007 |
| WO | WO 9826808 A2 | 6/1998 |
| WO | WO 9900093 A1 | 1/1999 |
| WO | WO 0036207 A1 | 6/2000 |
| WO | WO 0124840 A1 | 4/2001 |
| WO | WO 0134656 | 5/2001 |
| WO | WO 0183665 | 11/2001 |
| WO | WO 0192632 | 12/2001 |
| WO | WO 03006739 A1 | 1/2003 |
| WO | WO 03039602 A2 | 5/2003 |
| WO | WO 2004110193 A1 | 12/2004 |
| WO | WO 2005032252 A1 | 4/2005 |
| WO | WO 2006111991 A1 | 10/2006 |

OTHER PUBLICATIONS

American Society for Testing Materials (ASTM) Designation: E1164-02, "Standard Practice for Obtaining Spectrometric Data for Object-Color Evaluation," pp. 1-8, published Aug. 2002.

International Organization for Standardization (ISO) International Standard 7724/1, "Paints and Varnishes—Colorimetry—Part 1: Principles," First edition, 1984, 8 pages.

Japanese Industrial Standard, JIS Z 8722, "Methods of Colour Measurement—Reflecting and Transmitting Objects," 2000, 1-57 and 1 correction page, "Errata."

"CIE Publication No. 15.2," *Colorimetry*, Second Edition, 1986, pp. 1-74.

EP Search Report for 08807642.7 dated Dec. 6, 2010, 6 pages.

* cited by examiner

SELF-INDICATING WIPE FOR REMOVING BACTERIA FROM A SURFACE

BACKGROUND OF THE INVENTION

Many existing wipes are impregnated with a chemical solution (e.g., antimicrobial) for delivery to a contaminated surface. Unfortunately, however, such wipes may leave chemicals on the surface that are undesirable in certain applications. In response to these problems, a wipe was thus developed for simply removing bacteria from a surface. U.S. Patent Application Publication No. 2005/0137540 to Villanueva, et al., for instance, describes a wipe that has a positive charge through the use of cationic treatments, such as functionalized polymers, organic or inorganic oligomers, or particles coated with functionalized polymers, organic or inorganic oligomers. The treated wipe is able to remove a substantial amount of the bacteria from a surface. Although effective, one problem with such wipes is that they do not generally convey information to the user regarding the extent to which the wipe is removing bacteria. This can lead to a variety of problems, including continued wiping of a surface that is already sanitized. Moreover, the user may lack confidence that the wipe if effectively removing bacteria even when it is in fact functioning properly.

As such, a need currently exists for a wipe that is capable of removing bacteria from a surface, and at the same time, providing an indication to the user that the wipe is functioning properly.

SUMMARY OF THE INVENTION

In accordance with one embodiment of the present invention, a wipe for use in removing bacteria from a surface is disclosed that comprises a bacteriostatic agent and a solvatochromatic indicator. The bacteriostatic agent has an affinity for the negatively charged cell walls of the bacteria. Further, the solvatochromatic indicator undergoes a detectable color change in the presence of the bacteria.

Other features and aspects of the present invention are discussed in greater detail below.

DETAILED DESCRIPTION OF REPRESENTATIVE EMBODIMENTS

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Generally speaking, the present invention is directed to a wipe that includes a bacteriostatic agent that contains cations having an affinity for the negatively charged cell walls of bacteria. Gram positive bacteria, for example, contain teichoic acids that give the cell wall an overall negative charge due to the presence of phosphodiester bonds between teichoic acid monomers. Gram negative bacteria, on the other hand, contain highly charged lipopolysaccharides that may confer an overall negative charge to the cell wall. Regardless, the affinity of the bacteriostatic agent for the bacteria allows the wipe to capture bacteria, thereby removing them from a surface and also inhibiting their spread to other surfaces that may contact the wipe. Of particular advantage, the bacteriostatic agent may help protect against the spread or infection of pathogens without the use of chemicals, such as antiseptics or antibiotics. Still further, the wipe of the present invention also contains a solvatochromatic indicator that undergoes a color change in the presence of a broad spectrum of bacteria. Thus, when the wipe captures bacteria, the indicator undergoes a color change that signals to the user that the wipe is functioning properly. The lack of a color change may likewise provide the user with the assurance that the area is generally free of bacteria and clean.

Various embodiments of the present invention will now be described in more detail below.

I. Bacteriostatic Agent

The affinity of the bacteriostatic agent for the negatively charged walls of bacteria is typically due to the presence of cations that can electrostatically bind to the bacteria cell walls. The cations may, for instance, be metals, such as aluminium, iron, calcium, magnesium, etc., which are provided in the form of a metal salt. Suitable metal salts may include aluminium chlorohydrate, aluminum sulfate, calcium oxide, iron(III) chloride, iron(II) sulfate, sodium aluminate, sodium silicate, and so forth. If desired, the metal salt may be in the form of an oligomer or polymer. For example, aluminum chlorohydrate is an oligomeric metal salt that has the following formula:

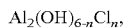

$$Al_2(OH)_{6-n}Cl_n,$$

wherein, n is from 1 to 5. Without intending to be limited by theory, it is believed that the cations of such salts may bind to the cell walls of bacteria and thus inhibit their release from the wipe. Further, when present in an aqueous solution, such metal salts may also act as a flocculant by reacting with water to form insoluble hydroxides which, upon precipitating, link together to form long chains or meshes (also referred to as "flocs"). These long chains or meshes may help physically trap bacteria, and thus further enhance the ability of the wipe to remove and retain bacteria.

Although the bacteriostatic agent is capable of binding to bacteria, the results may be improved by enhancing the contact efficiency between the bacteria and agent. One technique used to accomplish such enhanced contact efficiency involves increasing the effective surface area of the bacteriostatic agent. For example, particles may be employed that have a high surface area, such as from about 50 square meters per gram ($m^2/g$) to about 1000 $m^2/g$, in some embodiments from about 100 $m^2/g$ to about 600 $m^2/g$, and in some embodiments, from about 180 $m^2/g$ to about 240 $m^2/g$. Surface area may be determined by the physical gas adsorption (B.E.T.) method of Bruanauer, Emmet, and Teller, Journal of American Chemical Society, Vol. 60, 1938, p. 309, with nitrogen as the adsorption gas. The particles may possess various forms, shapes, and sizes depending upon the desired result. For instance, the particles may be in the shape of a sphere, crystal, rod, disk, tube, string, etc. Likewise, the average size of the particles is generally less than about 500 microns, in some embodiments less than about 100 microns, in some embodiments less than about 100 nanometers, in some embodiments from about 1 to about 50 nanometers, in some embodiments from about 2 to about 50 nanometers, and in some embodiments, from about 4 to about 20 nanometers. As used herein, the average size of a particle refers to its average length, width, height, and/or diameter. If desired, the particles may be relatively nonporous or solid. That is, the particles may have a pore volume that is less than about 0.5 milliliters per gram (ml/g), in some embodiments less than about 0.4 milliliters per gram, in some embodiments less than about 0.3 ml/g, and in some embodiments, from about 0.2 ml/g to about 0.3 ml/g. It is believed that the solid nature, i.e., low pore volume, of the particles may enhance the uniformity and stability of the particles.

Any of a variety of particles may be used to provide the desired increase in effective surface area, so long as they do not adversely interfere with the ability of the bacteriostatic agent to bind to bacteria. For instance, naturally occurring particles, such as nuclei, mycoplasma, plasmids, plastids, mammalian cells (e.g., erythrocyte ghosts), unicellular microorganisms (e.g., bacteria), polysaccharides (e.g., agarose), and so forth, may be used. Further, synthetic particles may also be utilized. For example, in one embodiment, latex particles may be employed, such as those formed from polystyrene, butadiene styrenes, styreneacrylic-vinyl terpolymer, polymethylmethacrylate, polyethylmethacrylate, styrene-maleic anhydride copolymer, polyvinyl acetate, polyvinylpyridine, polydivinylbenzene, polybutyleneterephthalate, acrylonitrile, vinylchloride-acrylates, and so forth, or an aldehyde, carboxyl, amino, hydroxyl, or hydrazide derivative thereof. Still other suitable particles include inorganic oxide particles, such as silica, alumina, zirconia, magnesium oxide, titanium dioxide, iron oxide, zinc oxide, copper oxide, zeolites, clays (e.g., smectite clay), combinations thereof, and so forth. Various examples of such inorganic oxide particles are described in U.S. Patent Application Publication Nos. 2003/0203009 to MacDonald; 2005/0084412 to MacDonald, et al.; 2005/0085144 to MacDonald, et al.; 2005/0084464 to McGrath, et al.; 2005/0084474 to Wu, et al.; and 2005/0084438 to Do, et al., which are incorporated herein in their entirety by reference thereto for all purposes.

Although not required, the "zeta potential" of the particles may be selected to optimize their functionality and/or ability to bind bacteria or substrate. For example, the particles may possess a negative zeta potential, such as less than about 0 millivolts (mV), in some embodiments less than about −10 mV, and in some embodiments, less than about −20 mV. Commercially available examples of particles having a negative zeta potential include Snowtex-C, Snowtex-O, Snowtex-PS, and Snowtex-OXS, which are silica nanoparticles available from Nissan Chemical of Houston, Tex. Alternatively, the particles may have a zeta potential of greater than about +20 millivolts (mV), in some embodiments greater than about +30 mV, and in some embodiments, greater than about +40 mV. By possessing a positive surface charge, the particles are well suited for being affixed to fibers that carry a negative surface charge (e.g., cellulosic fibers) through ionic attraction. Depending upon the difference in charge between the particles and the surface of the fibers (including van der Waals forces), the bond in some applications may be relatively permanent and substantive. Consequently, the particles may be affixed to fibers without the use of chemical binders or other attachment structures.

A positive zeta potential may be imparted to the particles in a variety of different ways. In one embodiment, the particles are formed entirely from a positively charged material. For example, alumina particles may be used in with the present invention. Some suitable alumina particles are described in U.S. Pat. No. 5,407,600 to Ando, et al., which is incorporated herein in its entirety by reference thereto for all purposes. Further, examples of commercially available alumina particles include, for instance, Aluminasol 100, Aluminasol 200, and Aluminasol 520, which are available from Nissan Chemical Industries Ltd. Alternatively, the positive zeta potential may be imparted by a continuous or discontinuous coating present on the surface of a core material. In some instances, these particles may actually possess a better stability over various pH ranges than particles formed entirely from positively charged materials. In one particular embodiment, for example, the particles are formed from silica particles coated with alumina. A commercially available example of such alumina-coated silica particles is Snowtex-AK, which is available from Nissan Chemical of Houston, Tex.

If desired, the bacteriostatic agent may be applied to the wipe in the form of a formulation that contains a mobile carrier, such as a liquid, gas, gel, etc. In some embodiments, for instance, the carrier may be an aqueous solvent, such as water, as well as a non-aqueous solvent, such as glycols (e.g., propylene glycol, butylene glycol, triethylene glycol, hexylene glycol, polyethylene glycols, ethoxydiglycol, and dipropyleneglycol); alcohols (e.g., methanol, ethanol, n-propanol, and isopropanol); triglycerides; ethyl acetate; acetone; triacetin; acetonitrile, tetrahydrafuran; xylenes; formaldehydes (e.g., dimethylformamide, "DMF"); etc. Upon application, the formulation may be dried to remove the carrier and leave a residue of the bacteriostatic agent.

Other additives may also be employed in the formulation in conjunction with the bacteriostatic agent, particles, etc. Surfactants, for instance, may be employed in certain embodiments. Particularly desired surfactants are nonionic surfactants, such as ethoxylated alkylphenols, ethoxylated and propoxylated fatty alcohols, ethylene oxide-propylene oxide block copolymers, ethoxylated esters of fatty ($C_8$-$C_{18}$) acids, condensation products of ethylene oxide with long chain amines or amides, condensation products of ethylene oxide with alcohols, acetylenic diols, and mixtures thereof. Various specific examples of suitable nonionic surfactants include, but are not limited to, methyl gluceth-10, PEG-20 methyl glucose distearate, PEG-20 methyl glucose sesquistearate, $C_{11-15}$ pareth-20, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, an ethoxylated nonylphenol, ethoxylated octylphenol, ethoxylated dodecylphenol, or ethoxylated fatty ($C_6$-$C_{22}$) alcohol, including 3 to 20 ethylene oxide moieties, polyoxyethylene-20 isohexadecyl ether, polyoxyethylene-23 glycerol laurate, polyoxy-ethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxy-ethylene-6 tridecyl ether, laureth-2, laureth-3, laureth-4, PEG-3 castor oil, PEG 600 dioleate, PEG 400 dioleate, and mixtures thereof. Commercially available nonionic surfactants may include the SURFYNOL® range of acetylenic diol surfactants available from Air Products and Chemicals of Allentown, Pa. and the TWEEN® range of polyoxyethylene surfactants available from Fischer Scientific of Pittsburgh, Pa.

A binder may also be employed to facilitate the immobilization of the bacteriostatic agent on the wipe. For example, water-soluble organic polymers may be employed as binders, such as polysaccharides and derivatives thereof. Polysaccharides are polymers containing repeated carbohydrate units, which may be cationic, anionic, nonionic, and/or amphoteric. In one particular embodiment, the polysaccharide is a nonionic, cationic, anionic, and/or amphoteric cellulosic ether. Suitable nonionic cellulosic ethers may include, but are not limited to, alkyl cellulose ethers, such as methyl cellulose and ethyl cellulose; hydroxyalkyl cellulose ethers, such as hydroxyethyl cellulose, hydroxypropyl cellulose, hydroxypropyl hydroxybutyl cellulose, hydroxyethyl hydroxypropyl cellulose, hydroxyethyl hydroxybutyl cellulose and hydroxyethyl hydroxypropyl hydroxybutyl cellulose; alkyl hydroxyalkyl cellulose ethers, such as methyl hydroxyethyl cellulose, methyl hydroxypropyl cellulose, ethyl hydroxyethyl cellulose, ethyl hydroxypropyl cellulose, methyl ethyl hydroxyethyl cellulose and methyl ethyl hydroxypropyl cellulose; and so forth.

Although the exact quantity of the bacteriostatic agent employed may vary based on a variety of factors, including the presence of other additives, the suspected concentration of the microorganism, etc., it is typically present in the formulation in an amount from about 0.01 wt. % to about 5 wt. %, in some embodiments from about 0.1 wt. % to about 4 wt. %, and in some embodiments, from about 0.5 wt. % to about 3 wt. %. Further, the bacteriostatic agent may also constitute from about 0.5 wt. % to about 20 wt. %, in some embodiments from about 1 wt. % to about 15 wt. %, and in some embodiments from about 2 wt. % to about 10 wt. %, based on the dry weight of the wipe.

II. Solvatochromatic Indicator

As indicated above, a solvatochromatic indicator is employed in the present invention that undergoes a color change in the presence of a broad spectrum of bacteria. Merocyanine indicators (e.g., mono-, di-, and tri-merocyanines), for instance, are one type of solvatochromatic indicator that may be employed. Merocyanine indicators, such as merocyanine 540, fall within the donor-simple acceptor indicator classification of Griffiths as discussed in "Colour and Constitution of Organic Molecules" Academic Press, London (1976). More specifically, merocyanine indicators have a basic nucleus and acidic nucleus separated by a conjugated chain having an even number of methine carbons. Such indicators possess a carbonyl group that acts as an electron acceptor moiety. The electron acceptor is conjugated to an electron donating group, such as a hydroxyl or amino group. The merocyanine indicators may be cyclic or acyclic (e.g., vinylalogous amides of cyclic merocyanine indicators). For example, cyclic merocyanine indicators generally have the following structure:

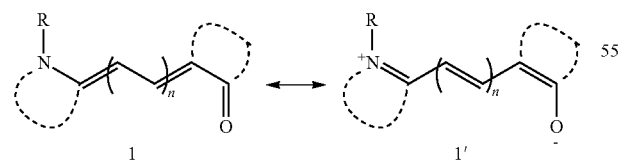

wherein, n is any integer, including 0. As indicated above by the general structures 1 and 1', merocyanine indicators typically have a charge separated (i.e., "zwitterionic") resonance form. Zwitterionic indicators are those that contain both positive and negative charges and are net neutral, but highly charged. Without intending to be limited by theory, it is believed that the zwitterionic form contributes significantly to the ground state of the indicator. The color produced by such indicators thus depends on the molecular polarity difference between the ground and excited state of the indicator. One particular example of a merocyanine indicator that has a ground state more polar than the excited state is set forth below as structure 2.

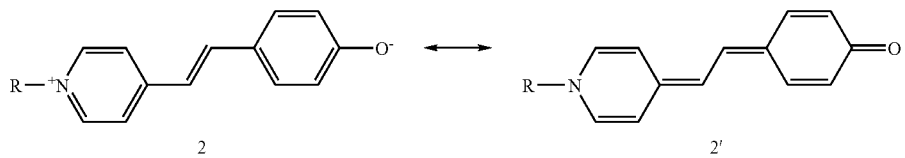

The charge-separated left hand canonical 2 is a major contributor to the ground state whereas the right hand canonical 2' is a major contributor to the first excited state. Still other examples of suitable merocyanine indicators are set forth below in the following structures 3-13.

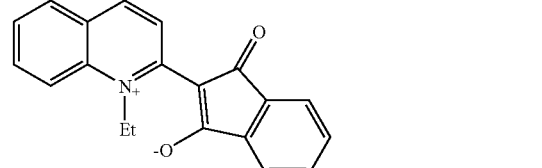

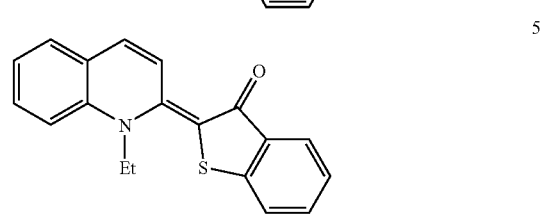

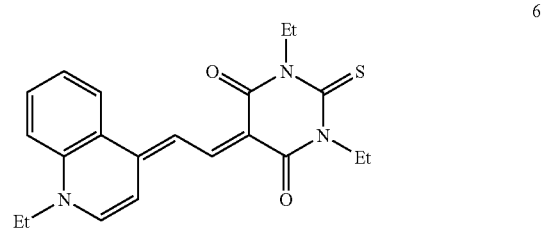

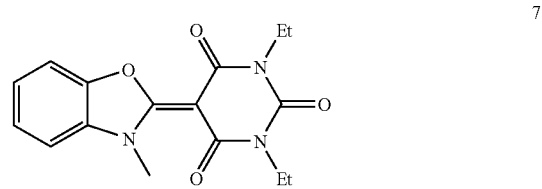

-continued

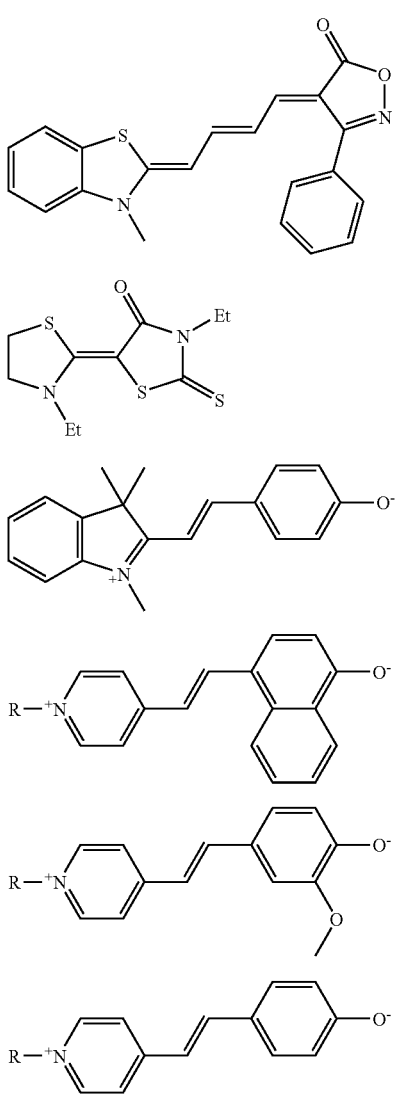

wherein, "R" is a group, such as methyl, alkyl, aryl, phenyl, etc.

Indigo is another example of a suitable solvatochromatic indicator for use in the present invention. Indigo has a ground state that is significantly less polar than the excited state. For example, indigo generally has the following structure 14:

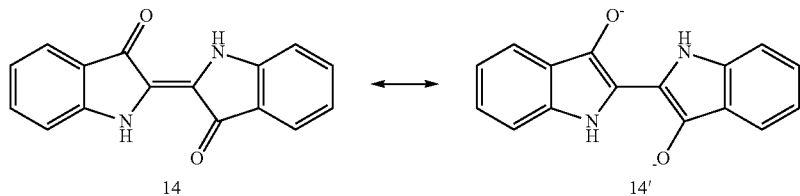

The left hand canonical form 14 is a major contributor to the ground state of the indicator, whereas the right hand canonical 14' is a major contributor to the excited state.

Other suitable solvatochromatic indicators that may be used in the present invention include those that possess a permanent zwitterionic form. That is, these indicators have formal positive and negative charges contained within a contiguous π-electron system. Contrary to the merocyanine indicators referenced above, a neutral resonance structure cannot be drawn for such permanent zwifterionic indicators. Exemplary indicators of this class include N-phenolate betaine indicators, such as those having the following general structure:

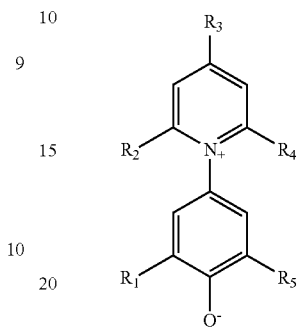

wherein $R_1$-$R_5$ are independently selected from the group consisting of hydrogen, a nitro group (e.g., nitrogen), a halogen, or a linear, branched, or cyclic $C_1$ to $C_{20}$ group (e.g., alkyl, phenyl, aryl, pyridinyl, etc.), which may be saturated or unsaturated and unsubstituted or optionally substituted at the same or at different carbon atoms with one, two or more halogen, nitro, cyano, hydroxy, alkoxy, amino, phenyl, aryl, pyridinyl, or alkylamino groups. For example, the N-phenolate betaine indicator may be 4-(2,4,6-triphenylpyridinium-1-yl)-2,6-diphenylphenolate (Reichardt's dye) having the following general structure 15:

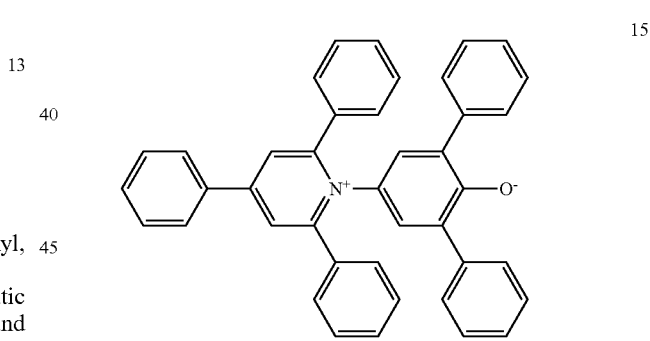

Reichardt's dye shows strong negative solvatochromism and may thus undergo a significant color change from blue to colorless in the presence of bacteria. That is, Reichardt's dye displays a shift in absorbance to a shorter wavelength and thus has visible color changes as solvent eluent strength (polarity) increases. Still other examples of suitable negatively solvatochromatic pyridinium N-phenolate betaine indicators are set forth below in structures 16-23:
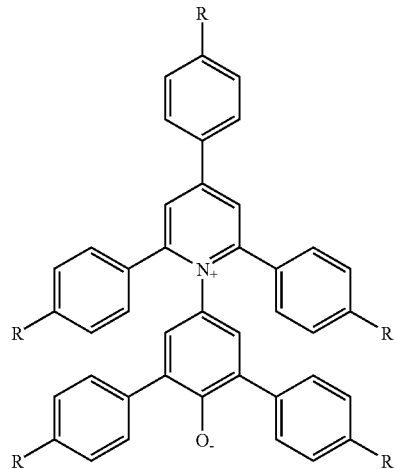
16
wherein, R is hydrogen, —C(CH$_3$)$_3$, —CF$_3$, or C$_6$F$_{13}$.
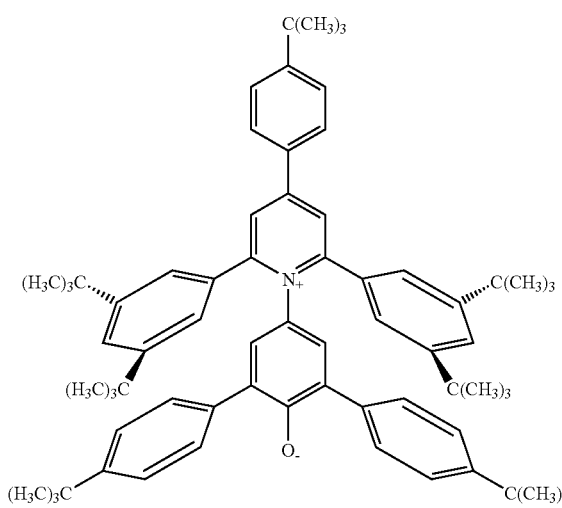
17
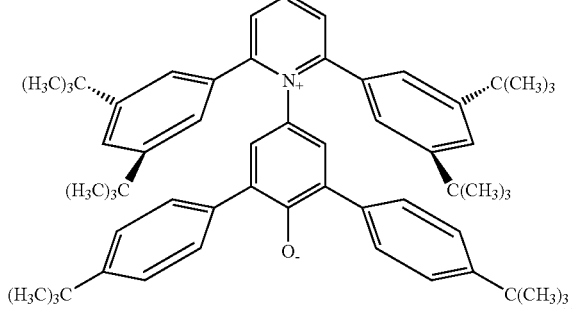
18
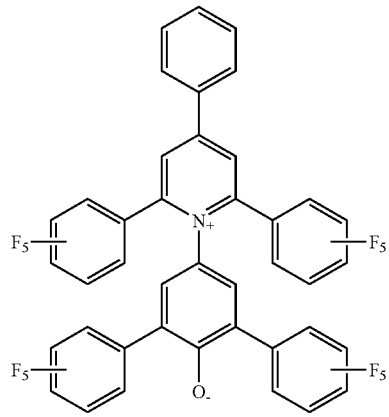
19
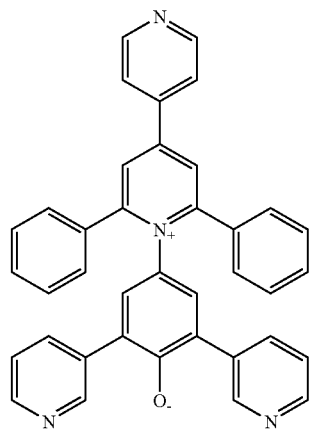
20
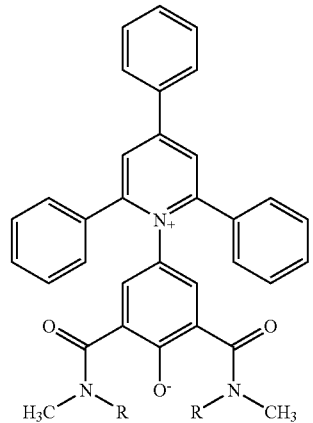
21
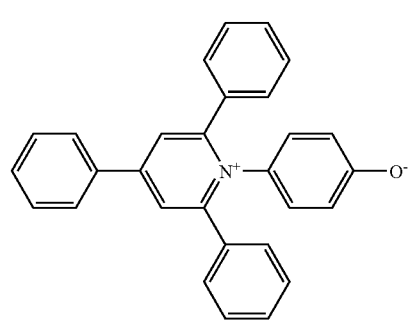
22

-continued

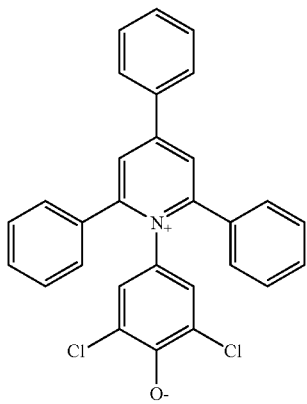
23

Still additional examples of indicators having a permanent zwitterionic form include indicators having the following general structure 24:

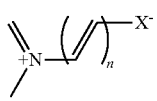
24 wherein, n is 0 or greater, and X is oxygen, carbon, nitrogen, sulfur, etc. Particular examples of the permanent zwitterionic indicator shown in structure 24 include the following structures 25-33.

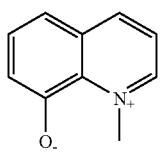
25

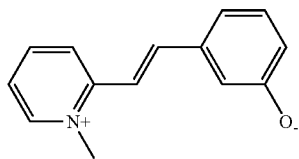
26

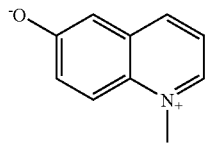
27

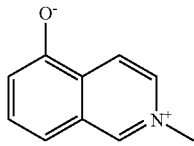
28

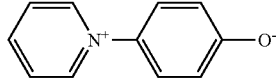
29

-continued

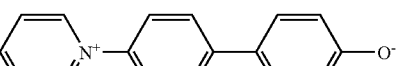
30

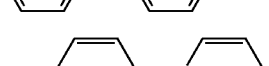
31

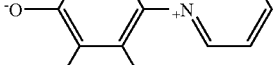
32

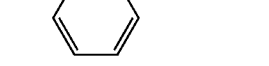
33

Still other suitable solvatochromatic indicators may include, but are not limited to 4-dicyanmethylene-2-methyl-6-(p-dimethylaminostyryl)-4H-pyran (DCM); 6-propionyl-2-(dimethylamino)naphthalene (PRODAN); 9-(diethylamino)-5H-benzo[a]phenox-azin-5-one (Nile Red); 4-(dicyanovinyl)julolidine (DCVJ); phenol blue; stilbazolium indicators; coumarin indicators; ketocyanine indicators; N,N-dimethyl-4-nitroaniline (NDMNA) and N-methyl-2-nitroaniline (NM2NA); Nile blue; 1-anilinonaphthalene-8-sulfonic acid (1,8-ANS), and dapoxylbutylsulfonamide (DBS) and other dapoxyl analogs. Besides the above-mentioned indicators, still other suitable indicators that may be used in the present invention include, but are not limited to, 4-[2-N-substituted-1,4-hydropyridin-4-ylidine)ethylidene]cyclohexa-2,5-dien-1-one, red pyrazolone indicators, azomethine indicators, indoaniline indicators, and mixtures thereof.

Although the above-referenced indicators are classified as solvatochromic, it should be understood that the present invention is not necessarily limited to any particular mechanism for the color change of the indicator. Even when a solvatochromic indicator is employed, other mechanisms may actually be wholly or partially responsible for the color change of the indicator. For example, acid-base or proton donation reactions between the indicator and microbe may result in the color change. As an example, highly organized acid moieties on bacteria cell walls may protonate certain indicators, resulting in a loss of color. Redox reactions between the indicator and microbe may likewise contribute to the color change.

The indicator may be applied to the wipe in the form of a formulation that contains a mobile carrier, surfactants, binders, etc., such as described above. The exact quantity of the indicator employed may vary based on a variety of factors, including the sensitivity of the indicator, the presence of other additives, the desired degree of detectability (e.g., with an unaided eye), the suspected concentration of the microorganism, etc. In some cases, it is desirable to only detect the presence of bacteria at a pathogenic concentration. For example, a bacterial concentration of about $1 \times 10^3$ colony forming units ("CFU") per milliliter of growth media or more, in some embodiments about $1 \times 10^5$ CFU/ml or more, in some embodiments about $1 \times 10^6$ CFU/ml or more, and in some embodiments, about $1 \times 10^7$ CFU/ml or more may be considered pathogenic. It should be understood that such concentrations may correlate to a liquid sample or a non-liquid sample that is cultured in a growth media. Regardless, the indicator may be employed in an amount sufficient to undergo a detectable color change in the presence of bacteria at a desired concentration. For instance, the indicator may be present in a formulation in an amount from about 0.01 wt. % to about 5 wt. %, in some embodiments from about 0.1 wt. % to about 4 wt. %, and in some embodiments, from about 0.5 wt. % to about 3 wt. %. Further, the indicator may also constitute from about 0.5 wt. % to about 20 wt. %, in some embodiments from about 1 wt. % to about 15 wt. %, and in some embodiments from about 2 wt. % to about 10 wt. %, based on the dry weight of the wipe.

III. Wipe

The wipe may be formed from any of a variety of materials as is well known in the art. In some embodiments, for example, the wipe may be a paper product containing one or more paper webs, such as facial tissue, bath tissue, paper towels, napkins, and so forth. The paper product may be single-ply in which the web forming the product includes a single layer or is stratified (i.e., has multiple layers), or multi-ply, in which the webs forming the product may themselves be either single or multi-layered. Normally, the basis weight of such a paper product is less than about 120 grams per square meter (gsm), in some embodiments less than about 80 gsm, in some embodiments less than about 60 grams per square meter, and in some embodiments, from about 10 to about 60 gsm.

Any of a variety of materials can also be used to form the paper web(s) of the product. For example, the material used to make the paper product may include absorbent fibers formed by a variety of pulping processes, such as kraft pulp, sulfite pulp, thermomechanical pulp, etc. The pulp fibers may include softwood fibers having an average fiber length of greater than 1 mm and particularly from about 2 to 5 mm based on a length-weighted average. Such softwood fibers can include, but are not limited to, northern softwood, southern softwood, redwood, red cedar, hemlock, pine (e.g., southern pines), spruce (e.g., black spruce), combinations thereof, and so forth. Exemplary commercially available pulp fibers suitable for the present invention include those available from Kimberly-Clark Corporation under the trade designations "Longlac-19". Hardwood fibers, such as eucalyptus, maple, birch, aspen, and so forth, can also be used. In certain instances, eucalyptus fibers may be particularly desired to increase the softness of the web. Eucalyptus fibers can also enhance the brightness, increase the opacity, and change the pore structure of the web to increase its wicking ability. Moreover, if desired, secondary fibers obtained from recycled materials may be used, such as fiber pulp from sources such as, for example, newsprint, reclaimed paperboard, and office waste. Further, other natural fibers can also be used in the present invention, such as abaca, sabai grass, milkweed floss, pineapple leaf, and so forth. In addition, in some instances, synthetic fibers can also be utilized.

If desired, the absorbent fibers (e.g., pulp fibers) may be integrated with synthetic fibers to form a composite. Synthetic thermoplastic fibers may also be employed in the nonwoven web, such as those formed from polyolefins, e.g., polyethylene, polypropylene, polybutylene, etc.; polytetrafluoroethylene; polyesters, e.g., polyethylene terephthalate and so forth; polyvinyl acetate; polyvinyl chloride acetate; polyvinyl butyral; acrylic resins, e.g., polyacrylate, polymethylacrylate, polymethylmethacrylate, and so forth; polyamides, e.g., nylon; polyvinyl chloride; polyvinylidene chloride; polystyrene; polyvinyl alcohol; polyurethanes; polylactic acid; copolymers thereof; and so forth. Because many synthetic thermoplastic fibers are inherently hydrophobic (i.e., non-wettable), such fibers may optionally be rendered more hydrophilic (i.e., wettable) by treatment with a surfactant solution before, during, and/or after web formation. Other known methods for increasing wettability may also be employed, such as described in U.S. Pat. No. 5,057,361 to Sayovitz, et al., which is incorporated herein in its entirety by reference thereto for all purposes. The relative percentages of such fibers may vary over a wide range depending on the desired characteristics of the composite. For example, the composite may contain from about 1 wt. % to about 60 wt. %, in some embodiments from 5 wt. % to about 50 wt. %, and in some embodiments, from about 10 wt. % to about 40 wt. % synthetic polymeric fibers. The composite may likewise contain from about 40 wt. % to about 99 wt. %, in some embodiments from 50 wt. % to about 95 wt. %, and in some embodiments, from about 60 wt. % to about 90 wt. % absorbent fibers.

Composites, such as described above, may be formed using a variety of known techniques. For example, a nonwoven composite may be formed that is a "coform material" that contains a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic and/or organic absorbent materials, treated polymeric staple fibers and so forth. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein in their entirety by reference thereto for all purposes. Alternatively, the nonwoven composite may be formed be formed by hydraulically entangling fibers and/or filaments with high-pressure jet streams of water. Hydraulically entangled nonwoven composites of staple length fibers and continuous filaments are disclosed, for example, in U.S. Pat. No. 3,494,821 to Evans and U.S. Pat. No. 4,144,370 to Bouolton, which are incorporated herein in their entirety by reference thereto for all purposes. Hydraulically entangled nonwoven composites of a continuous filament nonwoven web and pulp fibers are disclosed, for example, in U.S. Pat. No. 5,284,703 to Everhart, et al. and U.S. Pat. No. 6,315,864 to Anderson, et al., which are incorporated herein in their entirety by reference thereto for all purposes.

Regardless of the materials or processes utilized to form the wipe, the basis weight of the wipe is typically from about 20 to about 200 grams per square meter (gsm), and in some embodiments, between about 35 to about 100 gsm. Lower basis weight products may be particularly well suited for use as light duty wipes, while higher basis weight products may be better adapted for use as industrial wipes.

The wipe may assume a variety of shapes, including but not limited to, generally circular, oval, square, rectangular, or irregularly shaped. Each individual wipe may be arranged in a folded configuration and stacked one on top of the other to provide a stack of wet wipes. Such folded configurations are well known to those skilled in the art and include c-folded, z-folded, quarter-folded configurations and so forth. For example, the wipe may have an unfolded length of from about 2.0 to about 80.0 centimeters, and in some embodiments, from about 10.0 to about 25.0 centimeters. The wipes may likewise have an unfolded width of from about 2.0 to about 80.0 centimeters, and in some embodiments, from about 10.0 to about 25.0 centimeters. The stack of folded wipes may be placed in the interior of a container, such as a plastic tub, to provide a package of wipes for eventual sale to the consumer. Alternatively, the wipes may include a continuous strip of material which has perforations between each wipe and which may be arranged in a stack or wound into a roll for dispensing. Various suitable dispensers, containers, and systems for delivering wipes are described in U.S. Pat. No. 5,785,179 to Buczwinski, et al.; U.S. Pat. No. 5,964,351 to Zander; U.S. Pat. No. 6,030,331 to Zander; U.S. Pat. No. 6,158,614 to Haynes, et al.; U.S. Pat. No. 6,269,969 to Huang, et al.; U.S. Pat. No. 6,269,970 to Huang, et al.; and U.S. Pat. No. 6,273,359 to Newman, et al., which are incorporated herein in their entirety by reference thereto for all purposes.

In certain embodiments of the present invention, the wipe is a "wet wipe" in that it contains a solution for cleaning, disinfecting, sanitizing, etc. The particular wet wipe solutions are not critical and are described in more detail in U.S. Pat. No. 6,440,437 to Krzysik, et al.; U.S. Pat. No. 6,028,018 to Amundson, et al.; U.S. Pat. No. 5,888,524 to Cole; U.S. Pat. No. 5,667,635 to Win, et al.; and U.S. Pat. No. 5,540,332 to Kopacz, et al., which are incorporated herein in their entirety by reference thereto for all purposes. The amount of the wet wipe solution employed may depending upon the type of wipe material utilized, the type of container used to store the wipes, the nature of the cleaning formulation, and the desired end use of the wipes. Generally, each wipe contains from about 150 to about 600 wt. % and desirably from about 300 to about 500 wt. % of a wet wipe solution based on the dry weight of the wipe.

The bacteriostatic agent and/or indicator may be incorporated into the wipe during its formation or simply coated onto all or a portion of a surface of the wipe using known techniques, such as printing, dipping, spraying, melt extruding, coating (e.g., solvent coating, powder coating, brush coating, etc.), and so forth. Furthermore, the bacteriostatic agent and/or indicator may be applied together or separately to the wipe. In one embodiment, for example, a formulation is applied to the wipe (e.g., by dipping, spraying, or printing) that contains both the bacteriostatic agent and the indicator. Alternatively, a formulation is applied to the wipe (e.g., by dipping) that contains the bacteriostatic agent, and thereafter a formulation is applied to the wipe (e.g., by printing) that contains the indicator.

If desired, the formulation(s) may be applied in a pattern that covers from about 5% to about 95%, in some embodiments from about 10% to about 90%, and in some embodiments, from about 20% to about 75% of a surface of the wipe. The patterned application of the bacteriostatic agent and/or indicator may have various benefits, including enhanced aesthetic appeal, improved absorbency, etc. The particular type or style of the pattern is not a limiting factor of the invention, and may include, for example, any arrangement of stripes, bands, dots, or other geometric shape. The pattern may include indicia (e.g., trademarks, text, and logos), floral designs, abstract designs, any configuration of artwork, etc. It should be appreciated that the "pattern" may take on virtually any desired appearance.

A variety of techniques may be used for applying the formulation(s) in the desired pattern. For instance, the formulation(s) may be applied using rotogravure or gravure printing, either direct or indirect (offset). Gravure printing encompasses several well-known engraving techniques, such as mechanical engraving, acid-etch engraving, electronic engraving and ceramic laser engraving. Such printing techniques provide excellent control of the composition distribution and transfer rate. Gravure printing may provide, for example, from about 10 to about 1000 deposits per lineal inch of surface, or from about 100 to about 1,000,000 deposits per square inch. Each deposit results from an individual cell on a printing roll, so that the density of the deposits corresponds to the density of the cells. A suitable electronic engraved example for a primary delivery zone is about 200 deposits per lineal inch of surface, or about 40,000 deposits per square inch. By providing such a large number of small deposits, the uniformity of the deposit distribution may be enhanced. Also, because of the large number of small deposits applied to the surface of the substrate, the deposits more readily resolidify on the exposed fiber portions. Suitable gravure printing techniques are also described in U.S. Pat. No. 6,231,719 to Garvey, et al., which is incorporated herein in its entirety by reference thereto for all purposes. Moreover, besides gravure printing, it should be understood that other printing techniques, such as flexographic printing, may also be used.

Still another suitable contact printing technique that may be utilized in the present invention is "screen printing." Screen printing is performed manually or photomechanically. The screens may include a silk or nylon fabric mesh with, for instance, from about 40 to about 120 openings per lineal centimeter. The screen material is attached to a frame and stretched to provide a smooth surface. The stencil is applied to the bottom side of the screen, i.e., the side in contact with the substrate upon which the formulation(s) are to be printed. The formulation(s) are painted onto the screen, and transferred by rubbing the screen (which is in contact with the substrate) with a squeegee.

Ink-jet printing techniques may also be employed in the present invention. Ink-jet printing is a non-contact printing technique that involves forcing the ink through a tiny nozzle (or a series of nozzles) to form droplets that are directed toward the substrate. Two techniques are generally utilized, i.e., "DOD" (Drop-On-Demand) or "continuous" ink-jet printing. In continuous systems, ink is emitted in a continuous stream under pressure through at least one orifice or nozzle. The stream is perturbed by a pressurization actuator to break the stream into droplets at a fixed distance from the orifice. DOD systems, on the other hand, use a pressurization actuator at each orifice to break the ink into droplets. The pressurization actuator in each system may be a piezoelectric crystal, an acoustic device, a thermal device, etc. The selection of the type of ink jet system varies on the type of material to be printed from the print head. For example, conductive materials are sometimes required for continuous systems because the droplets are deflected electrostatically.

In addition to the printing techniques mentioned above, any other suitable application technique may be used in the present invention. For example, other suitable printing techniques may include, but not limited to, such as laser printing, thermal ribbon printing, piston printing, spray printing, flexographic printing, etc. Still other suitable application techniques may include bar, roll, knife, curtain, spray, slot-die, dip-coating, drop-coating, extrusion, stencil application, etc. Such techniques are well known to those skilled in the art.

As a result of the present invention, it has been discovered that a wipe may be employed to remove bacteria from a surface. The presence of the bacteria may then be revealed to the user through a detectable color change of the indicator. Several relevant bacterial groups that may be detected in the present invention include, for instance, gram negative rods (e.g., Entereobacteria); gram negative curved rods (e.g., vibious, *Heliobacter, Campylobacter*, etc.); gram negative cocci (e.g., *Neisseria*); gram positive rods (e.g., *Bacillus, Clostridium, Listeria*, etc.); gram positive cocci (e.g., *Staphylococcus, Streptococcus*, etc.); obligate intracellular parasites (e.g., *Ricckettsia* and *Chlamydia*); acid fast rods (e.g., *Myo-*

*bacterium, Nocardia*, etc.); spirochetes (e.g., *Treponema, Borellia*, etc.); and mycoplasmas (i.e., tiny bacteria that lack a cell wall). Particularly relevant bacteria include *E. coli* (gram negative rod), *Klebsiella pneumonia* (gram negative rod), *Streptococcus* (gram positive cocci), *Salmonella choleraesuis* (gram negative rod), *Listeria monocytogenes* (gram positive rod), *Staphyloccus aureus* (gram positive cocci), and *Pseudomonas aeruginosa* (gram negative rod).

The color change may be rapid and may be detected within a relatively short period of time. For example, the change may occur in about 5 minutes or less, in some embodiments about 1 minute or less, in some embodiments about 30 seconds or less, in some embodiments about 20 seconds or less, and in some embodiments, from about 10 seconds to about 2 minutes. Conversely, the color change could be used to monitor the build up of microbial contamination on the wipe over time. They could also come from contamination after use through contact with infected hands, etc. Thus, the color change may indicate an instant contamination of a high number of microbes present or the build-up of microbes on or in the wipe over time.

Regardless of when it occurs, the extent of the color change may be determined either visually or using instrumentation (e.g., optical reader) and provide a "real-time" indication of infection at a wound or incision site. The extent of the color change may be represented by a certain change in the absorbance reading as measured using a conventional test known as "CIELAB", which is discussed in *Pocket Guide to Digital Printing* by F. Cost, Delmar Publishers, Albany, N.Y. ISBN 0-8273-7592-1 at pages 144 and 145. This method defines three variables, $L^*$, $a^*$, and $b^*$, which correspond to three characteristics of a perceived color based on the opponent theory of color perception. The three variables have the following meaning:

$L^*$=Lightness (or luminosity), ranging from 0 to 100, where 0=dark and 100=light;

$a^*$=Red/green axis, ranging approximately from −100 to 100; positive values are reddish and negative values are greenish; and $b^*$=Yellow/blue axis, ranging approximately from −100 to 100; positive values are yellowish and negative values are bluish.

Because CIELAB color space is somewhat visually uniform, a single number may be calculated that represents the difference between two colors as perceived by a human. This difference is termed $\Delta E$ and calculated by taking the square root of the sum of the squares of the three differences ($\Delta L^*$, $\Delta a^*$, and $\Delta b^*$) between the two colors. In CIELAB color space, each $\Delta E$ unit is approximately equal to a "just noticeable" difference between two colors. CIELAB is therefore a good measure for an objective device-independent color specification system that may be used as a reference color space for the purpose of color management and expression of changes in color. Using this test, color intensities ($L^*$, $a^*$, and $b^*$) may thus be measured using, for instance, a handheld spectrophotometer from Minolta Co. Ltd. of Osaka, Japan (Model # CM2600d). This instrument utilizes the D/8 geometry conforming to CIE No. 15, ISO 7724/1, ASTME1164 and JIS Z8722-1982 (diffused illumination/8-degree viewing system. The D65 light reflected by the specimen surface at an angle of 8 degrees to the normal of the surface is received by the specimen-measuring optical system. Typically, the indicator undergoes a color change that is represented by a $\Delta E$ of about 2 or more, in some embodiments about 3 or more, and in some embodiments, from about 5 to about 50.

The present invention may be better understood with reference to the following examples.

EXAMPLE 1

A wire-textured coform laminate (WTCL) was treated with aluminum chlorohydrate (1% W/W) using a dip and nip procedure, with a resulting add-on of approximately 6 to 7%. The treated WTCL was then treated with a 1% solution of Reichardt's dye indicator (prepared in acetonitrile) in a small dot pattern using a syringe. Control WTCL wipe material without aluminum chlorohydrate was also used for this experiment as a control. Two 100 microliter drops of $10^7$ CFU/ml *S. aureus* were placed onto a ceramic tile. Treated wipe and control material were both used to wipe the drop off of the tile. These wipes were then used to make an "X" onto clean tiles. These tiles were then sprayed with bacterial indicator solution (80 mg/10 mL acetonitrile) using a Chromist® spray can. The treated WTCL was then also sprayed with the indicator. Finally, the treated wipe (now clearly visible) containing the bacteria was once again used to wipe a clean area of tile. This area was then sprayed with the indicator. The "X" for the control was readily visible. The treated wipe (treated with aluminum chlorohydrate) clearly did not transfer bacteria to the clean tile, unlike the control material.

EXAMPLE 2

Sheets of VIVA® paper towels (Kimberly-Clark Corporation, Neenah Wis.) were placed on a flat surface, three sheets wide. A stainless steel grilling grate (Weber Company, purchased from Home Depot store) was placed onto top of the sheets. Next a 100-milliliter saturated solution of Reichardt's dye in isopropanol with 10 milliliters of potassium hydroxide was placed into a container and then sprayed (Chromist sprayer) over the grilling grate with the VIVA® towels underneath. The grilling grate was removed and the towels were hung in a fumehood and allowed to dry. The paper towels now had multiple parallel lines of the Reichardt's dye across the paper towel. The lines were 4 centimeters apart. Onto a cutting board surface (plastic cutting boards, Kroger grocery store) was applied light smears (3 cm×15 cm) of live culture yogurt. Next, the treated VIVA® paper towels were used to wipe the surface of the cutting board. Where the paper towel had contacted the contaminated surface, the color of the Reichardt's dye lines were rapidly discharged indicating microbial contamination of the surface.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A wipe for use in removing bacteria from a surface, the wipe comprising a nonwoven web that includes absorbent fibers, the web being treated with at least one bacteriostatic agent and at least one zwitterionic solvatochromatic indicator, wherein the bacteriostatic agent includes an aluminum chlorohydrate having cations with an affinity for the negatively charged cell walls of the bacteria that enables the bacteriostatic agent to capture bacteria from the surface, wherein the bacteriostatic agent is applied to a surface of the wipe, wherein the indicator is applied over the bacteriostatic agent, and wherein the indicator is present on a surface of the wipe in a pattern that covers from 5% to 95% of the surface so that a visible pattern is detectable in the presence of the bacteria, wherein the detected visible pattern signals to a user that the bacteriostatic agent is capturing bacteria.

2. The wipe of claim 1, wherein the zwitterionic indicator includes a merocyanine dye.

3. The wipe of claim 2, wherein the merocyanine dye has the following structure:

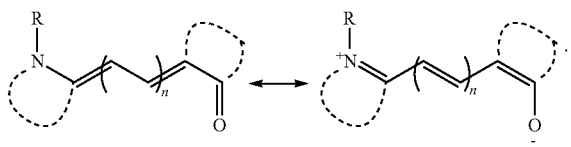

4. The wipe of claim 1, wherein the zwitterionic indicator includes an N-phenolate betaine dye.

5. The wipe of claim 4, wherein the N-phenolate betaine dye is Reichardt's dye.

6. The wipe of claim 1, wherein the bacteriostatic agent is formed from an aluminum chlorohydrate compound having the following formula:

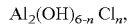

wherein, n is from 1 to 5.

7. The wipe of claim 1, wherein the bacteriostatic agent constitutes from 0.5 wt. % to 20 wt. % of the dry weight of the wipe.

8. The wipe of claim 1, wherein the indicator constitutes from 0.5 wt. % to 20 wt. % of the dry weight of the wipe.

9. The wipe of claim 1, wherein the wipe contains a wet wipe solution.

10. The wipe of claim 1, wherein the indicator produces a visually observable color change in the presence of *Escherichia coli, Klebsiella pneumonia, Streptococcus, Salmonella choleraesuis, Stiaphyloccus aureus, Pseudomonas aeruginosa, Listeria monocytogenes,* or a combination thereof.

11. The wipe of claim 1, wherein the nonwoven web is a paper web.

12. The wipe of claim 1, wherein the nonwoven web also contains synthetic thermoplastic fibers.

13. The wipe of claim 12, wherein the nonwoven web is a coform web.

14. The wipe of claim 1, wherein the indicator is present on a surface of the wipe in a pattern that covers from 20% to 75% of the surface.

* * * * *